(12) United States Patent
Ito et al.

(10) Patent No.: US 8,974,817 B2
(45) Date of Patent: Mar. 10, 2015

(54) TRANSDERMALLY ABSORBABLE PREPARATION

(75) Inventors: Takeshi Ito, Fukuoka (JP); Miho Ishigure, Sanuki (JP)

(73) Assignee: Teikoku Seiyaku Co., Ltd., Kagawa-Ken (JP)

( * ) Notice: Subject to any disclaimer, the term of this patent is extended or adjusted under 35 U.S.C. 154(b) by 34 days.

(21) Appl. No.: 12/934,425

(22) PCT Filed: Mar. 25, 2009

(86) PCT No.: PCT/JP2009/055965
§ 371 (c)(1),
(2), (4) Date: Jan. 21, 2011

(87) PCT Pub. No.: WO2009/119673
PCT Pub. Date: Oct. 1, 2009

(65) Prior Publication Data
US 2011/0104215 A1    May 5, 2011

(30) Foreign Application Priority Data

Mar. 25, 2008 (JP) ................................. 2008-077903

(51) Int. Cl.
*A61K 9/70* (2006.01)
*A61K 9/00* (2006.01)
(Continued)

(52) U.S. Cl.
CPC ............. *A61K 31/138* (2013.01); *A61K 9/7061* (2013.01); *A61K 9/7084* (2013.01)
USPC ............ 424/449; 400/400; 514/625; 514/570

(58) Field of Classification Search
CPC . A61K 31/138; A61K 9/7061; A61K 9/7084; A61K 47/10; A61K 31/16; A61K 31/19
USPC .......................... 424/400, 449; 514/625, 570
See application file for complete search history.

(56) References Cited

U.S. PATENT DOCUMENTS

| 4,573,996 A | 3/1986 | Kwiatek et al. |
| 4,605,548 A * | 8/1986 | Ushiyama et al. ............ 424/449 |

(Continued)

FOREIGN PATENT DOCUMENTS

| CN | 1633994 | 7/2005 |
| JP | 61-275213 | 12/1986 |

(Continued)

OTHER PUBLICATIONS

Chinese Office Action dated Sep. 26, 2011, issued in Chinese Application No. 200980114602.7 corresponding to present US Application, with English translation thereof.

(Continued)

*Primary Examiner* — Aradhana Sasan
(74) *Attorney, Agent, or Firm* — Wenderoth, Lind & Ponack, L.L.P (57) ABSTRACT

Disclosed is a novel transdermally absorbable preparation which enables the efficient, stable and long-term administration of a drug to a living body. More specifically, the transdermally absorbable preparation comprises: a laminate comprising an outer film, a drug-containing layer and a support layer laminated in this order from the side to be contacted with the skin; and a fixing means for fixing the laminate on the skin. In the transdermally absorbable preparation, the outer film is a drug-permeable polymer film that can control the release of the drug into the skin and is provided as a surface of the laminate which is to be contact with the skin.

4 Claims, 5 Drawing Sheets

(51) Int. Cl.
  *A61K 31/16* (2006.01)
  *A61K 31/19* (2006.01)
  *A61K 31/138* (2006.01)

(56) References Cited

U.S. PATENT DOCUMENTS

| | | | |
|---|---|---|---|
| 4,756,710 A | | 7/1988 | Bondi et al. |
| 4,765,986 A | * | 8/1988 | Liedtke .......................... 424/449 |
| 4,889,720 A | | 12/1989 | Konishi |
| 5,196,202 A | | 3/1993 | Konishi |
| 6,471,986 B1 | * | 10/2002 | Cline et al. .................... 424/446 |
| 2005/0142174 A1 | | 6/2005 | Assmus et al. |
| 2008/0233178 A1 | | 9/2008 | Reidenberg et al. |
| 2011/0104247 A1 | * | 5/2011 | Ito et al. ........................ 424/449 |

FOREIGN PATENT DOCUMENTS

| | | |
|---|---|---|
| JP | 63-060924 | 3/1988 |
| JP | 04-089429 | 3/1992 |
| JP | 07-069869 | 3/1995 |
| JP | 7-145061 | 6/1995 |
| JP | 2001-039873 | 2/2001 |
| JP | 2004-083523 | 3/2004 |
| JP | 2005-519054 | 6/2005 |
| JP | 2007-523167 | 8/2007 |
| JP | 2007-284378 | 11/2007 |
| WO | 02/069942 | 9/2002 |
| WO | 2006082728 | 8/2006 |
| WO | 2007/058190 | 5/2007 |

OTHER PUBLICATIONS

Form PCT/IB/338 together with English translation of International Preliminary Report on Patentability dated Nov. 25, 2010 in (PCT) Application No. PCT/JP2009/055965.
International Search Report issued May 26, 2009 in International (PCT) Application No. PCT/JP2009/055965.
Search Report issued Sep. 25, 2013 in corresponding European Application No. 09726157.2.
Office Action issued Mar. 7, 2014 in corresponding Japanese Application No. 2010-505733, with English translation.
Japanese Office Action mailed Sep. 20, 2013 in corresponding Japanese Application No. 2010-505733 with English translation.
Japanese Office Action mailed Sep. 24, 2013 in corresponding Japanese Application No. 2010-505734 with English translation.
Office Action issued Sep. 27, 2013 in corresponding Australian Application No. 2009229994.

* cited by examiner

F I G. 1

(A)　　　　　(B)　　　　　(C)

(D)　　　　　(E)　　　　　(F)

10

3

11

(G)

F I G. 2

F I G. 3

F I G. 4

F I G. 5

F I G. 6

TRANSDERMALLY ABSORBABLE PREPARATION

REFERENCE OF RELATED APPLICATIONS

The present application claims the benefit of priority from Japanese Patent Application No. 2008-077903 filed on Mar. 25, 2008, the entire disclosure of which is incorporated herein by reference.

FIELD OF THE INVENTION

The present invention relates to a transdermally absorbable preparation which enables the efficient, stable and long-term administration of a drug to a living body.

BACKGROUND OF THE INVENTION

Transdermally absorbable preparations have recently come into notice as the preparations for administering drugs to living bodies from the viewpoint of handling facility and dosage control. Dosage forms of the transdermally absorbable preparations mainly include transdermally absorbable preparations of reservoir type and matrix type.

The transdermally absorbable preparations of reservoir type are those which are provided with an adhesive layer, a release controlling membrane and a drug containing layer in order from the side of skin. For instance, it has been described in Japanese Patent Laid-Open Publication No. 2003-63954 that the releasability of a drug from an adhesive layer is improved by uniformly dispersing a particulate inorganic salt or a water soluble polymer into the adhesive layer of a transdermally absorbable preparation of reservoir type. However, it is necessary for the transdermally absorbable preparations of reservoir type to optimize the constitution of the adhesive layer by taking account of the nature and releasing period of the drug, which takes time and labor. Moreover, transdermally absorbable preparations of reservoir type have the problem that constituents including a drug are transferred to the adhesive layer with the passage of time resulting in the alteration of the physical properties of the adhesive layer and thus decreasing remarkably both the adherence ability onto skin and the drug releasing ability.

Further, transdermally absorbable preparations of matrix type are known as the preparations in which the adhesive layer contains a drug. Transdermally absorbable preparations of matrix type can be prepared easily as compared with those of reservoir type. However, it has been described in U.S. Pat. No. 6,465,004 that in transdermally absorbable preparations of matrix type the drug tends to be crystallized from the adhesive layer during its shelf life thus leading to the adherence ability onto skin and the decrease in the drug releasing ability. Moreover, in transdermally absorbable preparations of matrix type, the amounts of the constituents such as the drug and the absorption promoting agent are limited for maintaining their adherence ability onto skin.

Furthermore, exercise and bathing are generally limited during the actual use of a transdermally absorbable preparation in order to avoid its peeling off from the skin. However, it is difficult to avoid the decrease with the passage of time in the drug releasing ability and adhesion ability of the preparation in spite of such limitations. Thus, it has still been needed to create a transdermally absorbable preparation which enables the efficient, stable and long-term administration of a drug to a living body.

SUMMARY OF INVENTION

The present inventors have now obtained a novel transdermally absorbable preparation which enables the efficient, stable and long-term administration of a drug to a living body. The present invention is based on such findings.

Therefore, the object of the present invention is to provide a novel transdermally absorbable preparation which enables the efficient, stable and long-term administration of a drug to a living body.

Accordingly, the transdermally absorbable preparation according to the present invention is a transdermally absorbable preparation comprising a laminate comprising, in the order from the skin-contacting side, an outer membrane, a drug containing layer and a support layer and a fixing means for fixing the laminate on the skin, wherein the outer membrane is a drug permeable polymer membrane which ensures controlled release of the drug into the skin and is provided on the skin-contacting surface of the laminate.

According to the transdermally absorbable preparation of the present invention, a drug can be administered efficiently and stably to a living body for a long period.

BRIEF DESCRIPTION OF THE DRAWINGS

FIG. 3A is a sectional view of another suitable embodiment of the transdermally absorbable preparation according to the present invention in the manufacturing process. Figure B is a rear view showing another suitable transdermally absorbable preparation according to the present invention. Figure C is a sectional view of another suitable transdermally absorbable preparation according to the present invention on the skin.

DETAILED DESCRIPTION OF THE INVENTION

Transdermally Absorbable Preparation

The transdermally absorbable preparation according to the present invention is characterized in that a drug permeable polymer membrane is provided on the skin-contacting surface as described above. The transdermally absorbable preparation according to the present invention is excellent in the retaining stability of a drug and its adhesion stability on the skin, easily capable of controlling the drug releasing speed, so that it may be advantageously used for the efficient and stable administration of the drug to a living body for a long period.

Preferred embodiments of the transdermally absorbable preparation according to the present invention are now described with reference to the schematic illustrations.

Figure 1:
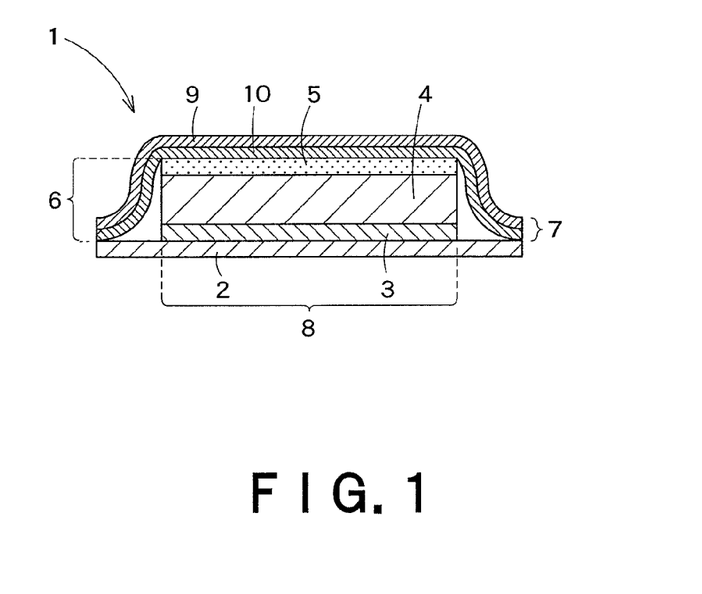
FIG. 1 is a sectional view of one embodiment of the transdermally absorbable preparation according to the present invention.

FIG. 1 is a sectional view of one embodiment of the transdermally absorbable preparation according to the present invention.

As shown in FIG. 1, the transdermally absorbable preparation 1 is provided with a laminate which comprises, in the order from the skin 2-contacting side, an outer membrane 3, a drug containing layer 4 and a support layer 5, and a fixing means 7 with which the laminate 6 can be fixed on the skin 2. Further, the outer membrane 3 is composed of a drug permeable polymer membrane which ensures controlled release of the drug into the skin 2 and is provided on the skin-contacting surface 8 of the laminate 6. It is an unexpected fact that the drug efficiently permeates the skin by only contacting the drug permeable polymer membrane with the skin directly without passing through an adhesive layer.

Further, in FIG. 1, a fixing means 7 comprises, in the order from the skin-contacting side, the adhesive layer 10 and the cover layer 9, and covers the region excluding the skin-contacting surface 8 of the laminate 6. The adhesive layer 10 adheres to the skin 2 at the peripheral and terminal regions of the skin-contacting surface 8 of the laminate 6 and fixes the transdermally absorbable preparation 1 on the skin 2. Such arrangement of the adhesive layer is advantageous to avoiding the transfer of the components including the drug from the drug containing layer to the adhesive layer resulting in the change of the physical properties of the adhesive layer with the passage of time and ensuring the stable adhesion of the transdermally absorbable preparations to the skin.

Furthermore, FIGS. 2A-G are rear views (at the contact side with the skin) which show suitable embodiments of the transdermally absorbable preparation according to the present invention.

Figure 2:
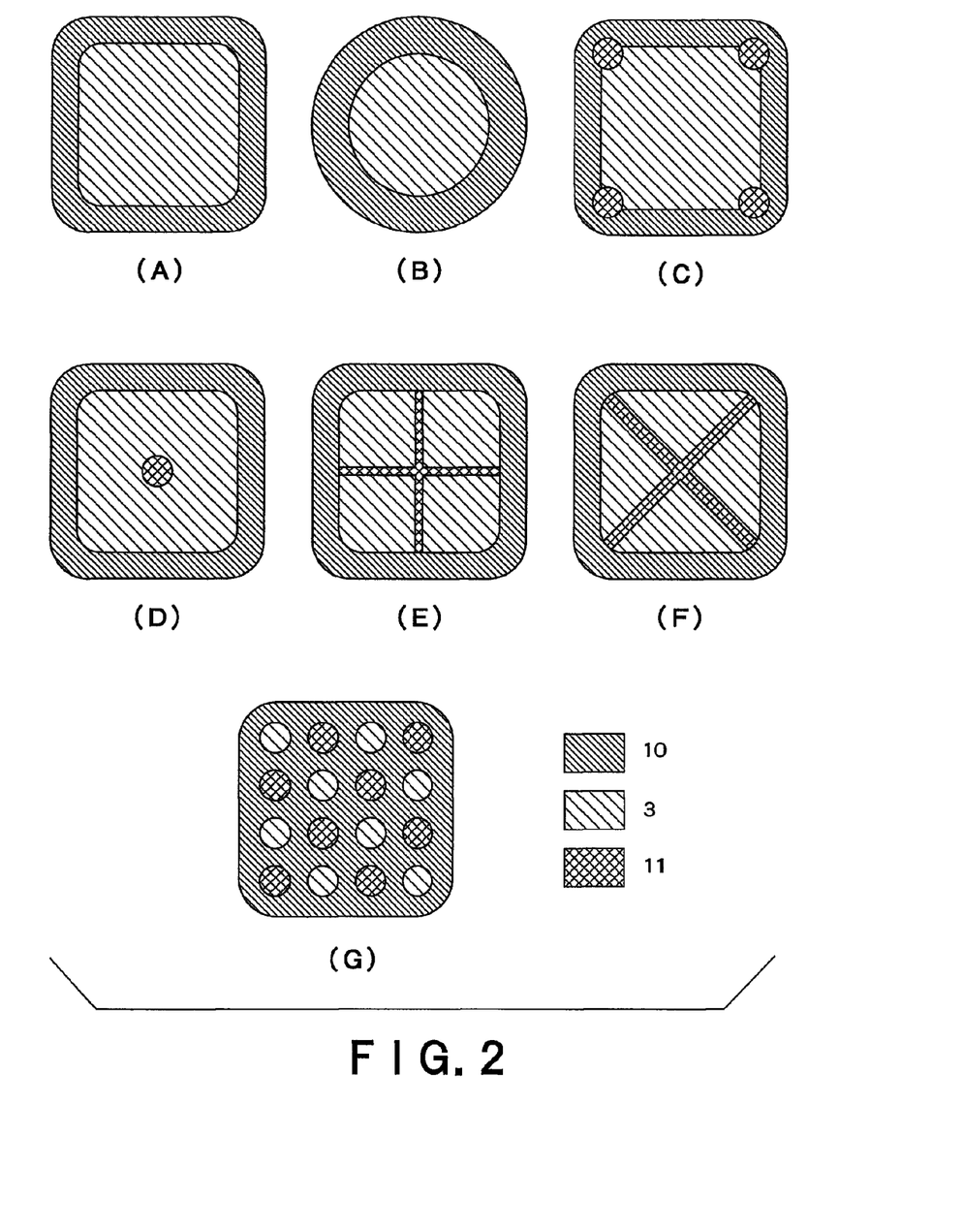
FIGS. 2A-G are the rear view of the suitable embodiments of the transdermally absorbable preparation according to the present invention.

As shown in FIGS. 2A and B, the rear area (the skin contact area) of the transdermally absorbable preparation comprises the outer membrane 3 and the adhesive layer 10 placed at the peripheral and terminal regions of outer membrane 3, and the outer membrane 3 is provided so that it can directly contact with the skin 2. The adhesive layer in the skin contact area of the transdermally absorbable preparation according to the present invention is, as described above, provided not at the whole area but at the peripheral and terminal regions of outer membrane, which is convenient for reducing the skin irritation on removing the transdermally absorbable preparation.

Further, as shown in FIGS. 2C-G, an auxiliary adhesive 11 may be optionally coated on the skin contact area of the outer membrane 3 in order to support the adhesion between the skin and the transdermally absorbable preparation. As shown in FIGS. 2C-G, the disposition of the auxiliary adhesive 11 may be appropriately changed as far as the outer membrane 3 can be directly contacted with the skin 2. Thus, the auxiliary adhesive 11 can be advantageously used for further improving the stability of the transdermally absorbable preparation on the skin. In this connection, a honeycomb structure in which the outer membrane 3 and the auxiliary adhesive 11 are alternately disposed on one skin side of the transdermally absorbable preparation, as shown in FIG. 2G, and the present invention also includes such embodiment.

In addition, a well known liner may also be placed on the skin contact area of the transdermally absorbable preparation, and the liner will be removed on the application of the preparation.

Furthermore, in FIGS. 3A-C, another preferred embodiments of the transdermally absorbable preparation according to the present invention which is excellent in the adhesion stability on the skin and the retaining stability of a drug are described with reference to schematic illustrations.

Figure 3:
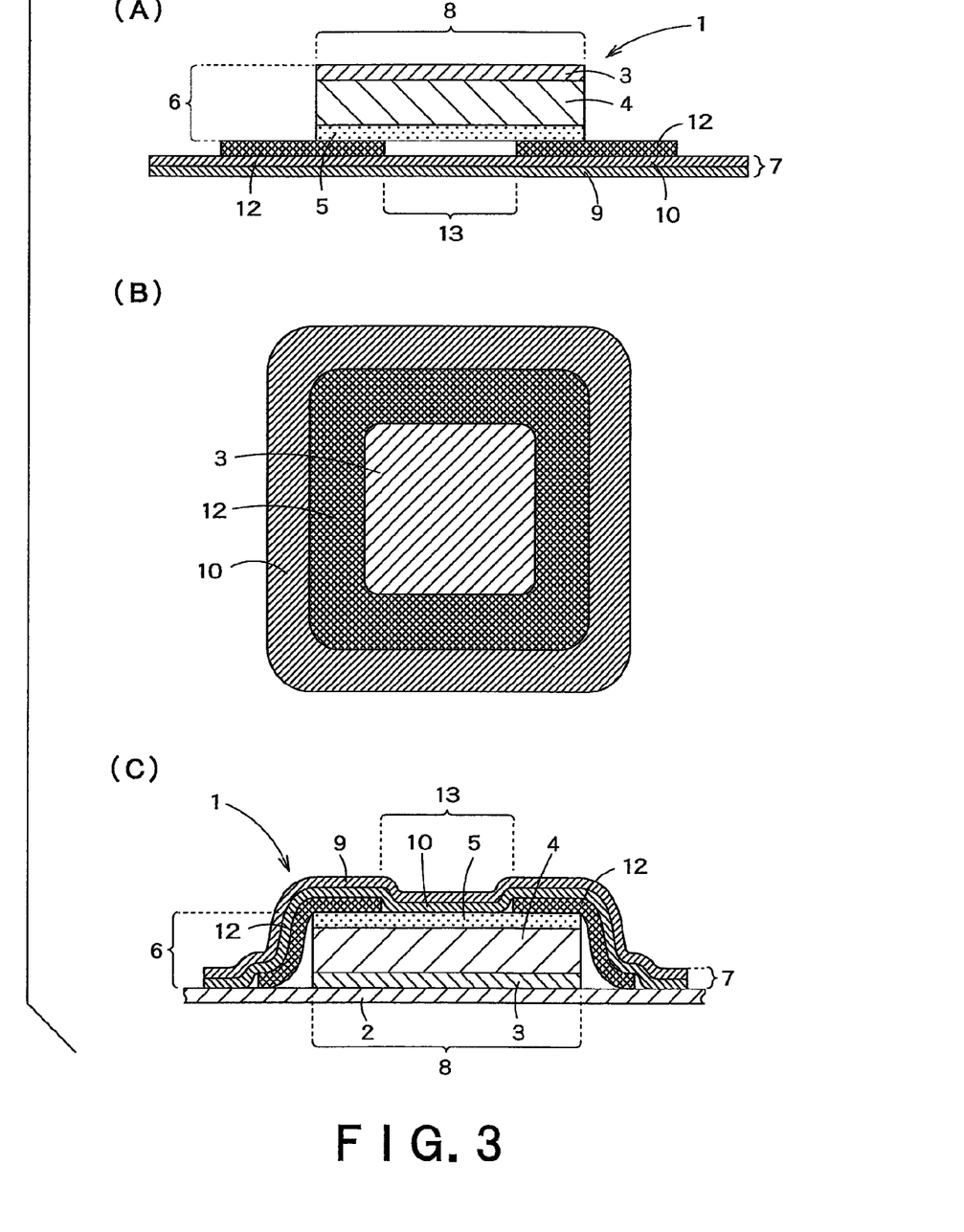

FIG. 3A shows the case in which respective layers are laminated in the preparation process of the transdermally absorbable preparation according to the present invention, and the transdermally absorbable preparation 1 is characterized by comprising an inner layer 12 between the laminate 6 and the fixing means 7. Furthermore, the inner layer 12 extends outward from the peripheral region of the support layer 5 on the fixing means 7. Further, the inner layer 12 is constructed in a ring form and has an inner hole 13.

Further, FIG. 3B is a rear elevation (at the skin contact area) of the aforementioned transdermally absorbable preparation 1 having an inner layer 12. In the skin contact area of the transdermally absorbable preparation 1, the adhesive layer 10, the inner layer 12 and the outer membrane 3 are disposed in the order from outer side.

Furthermore, FIG. 3C is a sectional view of the transdermally absorbable preparation 1 having an inner layer 12 on the skin. The inner layer 12 separates the drug containing layer 4 from the adhesive layer 10. Thus, the disposition of the inner layer 12 is advantageous to controlling the transfer of the drug to the adhesive layer and improving the adhesion stability of the transdermally absorbable preparation 1 and furthermore the retaining stability of a drug.

In addition, the adhesive layer 10 is directly in contact with the support layer 5 surrounded by the inner layer 12 via the inner hole 13 of the inner layer 12 so as to fix the laminate 6 from the inside. Such a construction is advantageous to stably fixing the laminate on the skin during the application period of the preparation.

In this connection, the support layer and the inner layer may be constructed either integrally or individually, and preferably constructed individually. It has been confirmed from the experiments conducted by the present inventors that the individual construction of the support layer and the inner layer is particularly advantageous to preventing the contact of the adhesive layer and the drug containing layer and the transfer of the components of the drug containing layer into the adhesive layer and accomplishing the improved storage stability of a drug and the stable skin absorption of a drug during application.

Further, the drug content of the drug containing layer in the transdermally absorbable preparation according to the present invention can be established without consideration of the adhesion to the skin unlike the conventional reservoir type or matrix type preparations. Such drug content is preferably established at a higher dosage in consideration of the long term administration. Specifically, the amount of a drug in the drug containing layer is preferably in the range of 15% by weight or more, more preferably in the range of 15-50% by weight.

The drug in the present invention can be appropriately determined in consideration of the disease, the condition of the subject, and the like.

Moreover, the drug may be a free body or a salt.

The specific examples of the drug include, but are not limited to, topical anesthetics such as bupivacaine hydrochloride and mepivacaine hydrochloride; antiepiloptics such as sodium valproate; analgesics such as morphine hydrochloride, fentanyl citrate and buprenorphine hydrochloride; antipyretic analgesics such as sulpyrine, antipyrine and acetaminophen; antipsychotics such as chloropromazine hydrochloride, levomepromazine hydrochloride and clocapramine hydrochloride; antidepressants such as imipramine hydrochloride, trazodone hydrochloride and fluvoxamine maleate; antianxiety agents such as diazepam, alprazolam and tandospirone citrate; tranquilizers such as hydroxyzine hydrochloride; brain function activating agents such as tiapride hydrochloride and protirelin tartrate; cerebral circulation activators such as isosorbide, pentoxifylline and fasudil hydrochloride; antiparkinsonean agents such as benserazide hydrochloride, amantazine hydrochloride and talipexole hydrochloride; muscle relaxants such as epirizone hydrochloride, tizanidine hydrochloride and tolperisone hydrochloride; antipeptic ulcer agents such as scopolamine butyl bromide, pirenzepine hydrochloride and timepidium bromide; antihistamines such as chlorophenylamine maleate, promethazine hydrochloride and cetirizine hydrochloride; chemical mediator release inhibitors such as emedastin fumarate, suplatast tosylate and epinastin hydrochloride; cardiopathy therapeutics such as aminophylline, diltiazem hydrochloride, nicorandil, propranolol hydrochloride, isoprenaline hydrochloride, disopyramide phosphate and procainamide hydrochloride; antihypertensives such as captopril, enarapril maleate, amosulalol hydrochloride, prazosin hydrochloride, urapidil and clonidine hydrochloride; vasodilators such as tolazoline hydrochloride; vasoconstrictors such as amezinium methyl sulfate, etilefrine hydrochloride, phenylefrine hydrochloride and midodrine hydrochloride; anti-hyperlipemic agents such as pravastatine sodium, fluvastatin sodium and cerivastatin sodium; antitussive expectorants such as dextromethorphan hydrobromide, fominoben hydrochloride and acetylcisteine; anti-asthmatic agents such as clenbuterol hydrochloride, fenoterol hydrobromide and procaterol; H2 blockers such as ranitidine hydrochloride and roxatidine acetate hydrochloride; proton pump inhibitors such as omeprazole, lansoprazole and rabeprazole; antiemetics such as granisetrone hydrochloride, azasetrone hydrochloride, ondansetrone hydrochloride and ramosetrone hydrochloride; nonsteroidal anti-inflammatory agents such as loxoprofen sodium, flurbiprofen, diclophenac sodium and tiaramide hydrochloride; antirheumatic agents such as bucillamine and penicillamine; urinary disease therapeutics such as oxybutynin hydrochloride, tamsulosine hydrochloride and propiverine hydrochloride; β-blockers such as bisoprolol fumarate and betaxolol hydrochloride.

The drug containing layer may contain, in addition to the drug, other materials including a base material in consideration of the drug retention.

The base material in the drug containing layer can be appropriately determined depending on the nature and content of the drug and is preferably dialkylaminoalkyl(meth)acrylate-alkyl(meth)acrylate-hydroxyalkyl(meth)acrylate copolymer, (meth)acrylate ester-vinyl ester copolymer, polyacrylate, polydimethylsiloxane, polyisobutylene, styrene-isoprene-styrene block copolymer, polyisoprene or a combination thereof, more preferably dialkylaminoalkyl(meth)acrylate-alkyl(meth)acrylate-hydroxyalkyl(meth)acrylate copolymer, (meth)acrylate ester-vinyl ester copolymer or a combination thereof, further preferably di-C1-12 alkylamino C1-10 alkyl(meth)acrylate-C1-10 alkyl(meth)acrylate copolymer, C1-10 alkyl(meth)acrylate-hydroxy C1-10 alkyl (meth)acrylate-glycidyl(meth)acrylate-vinyl acetate copolymer or a combination thereof, further preferably di-C1-6 alkylamino C1-6 alkyl(meth)acrylate-C1-8 alkyl(meth)acrylate copolymer, C1-12 alkyl(meth)acrylate-hydroxy C1-8 alkyl(meth)acrylate-glycidyl(meth)acrylate-vinyl acetate copolymer or a combination thereof, further preferably methyl(meth)acrylate-butyl(meth)acrylate-dimethylaminoethyl(meth)acrylate copolymer, 2-ethylhexyl acrylate-hydroxyethyl acrylate-glycidyl(meth)acrylate-vinyl acetate copolymer, or a combination thereof.

Further, the drug containing layer may further comprise an absorption promoting agent. Such absorption promoting agent can be appropriately selected depending on the nature and desired skin permeation rate of the drug, and preferably includes alcohol, organic acid, organic acid ester or a combination thereof, more preferably higher alcohol, polyhydric alcohol, divalent-tetravalent carboxylic acid, fatty acid, fatty acid ester, or a combination thereof, and further preferably C8-18 higher alcohol, divalent-trivaelent alcohol, C6-10 divalent-trivalent carboxylic acid, C7-19 fatty acid, sorbitan C7-19 fatty acid ester, C7-19 fatty acid C2-8 alkyl ester, or a combination thereof.

Further, a drug permeable polymer membrane constituting the outer membrane is directly placed on the skin, and thus the drug release rate in the transdermally absorbable preparation according to the present invention can be easily controlled depending on the drug permeable polymer membranes without regard to the nature of the adhesive layer unlike the conventional reservoir type or matrix type preparations.

The drug permeable polymer membrane is not specifically limited as far as it is capable of controlling the release of the drug onto the skin, but it is preferably a microporous membrane equipped with pores through which the drug can be permeated. The pore size and pore density of the microporous membrane can be appropriately determined in consideration of the desired factors including the skin permeation rate of the drug. For instance, the pore has an average pore size in the range of 0.03-0.25 µm. Further, the area of one skin side of the drug permeable membrane can be appropriately determined by taking the desired factors such as the drug release rate and adhering site.

Further, the constituent materials of the drug permeable polymer membrane preferably include EVA (ethylene-vinyl acetate copolymer), polyethylene, polypropylene, polyacrylonitrile, polymethyl methacrylate, or a combination thereof.

Furthermore, the inner layer is preferably used for separating the adhesive layer of the fixing means and the drug containing layer in the transdermally absorbable preparation according to the present invention.

The materials of such inner layers preferably include drug impermeable materials, specifically polyethylene terephthalate, polyester, polyethylene, polyurethane, polyamide, polypropylene, and ethylene-vinyl acetate copolymer.

Further, the support layer can be constructed with the same materials as the inner layer.

Further, the constituent material of the cover layer may be either stretchable or unstretchable, but it is preferably a drug impermeable material. The materials constructing the cover layer specifically include woven fabric, unwoven fabric, PET (polyethylene terephthalate), polyurethane, polyester, polyethylene, or combined materials thereof.

Further, the adhesive layer includes without limitation thereto biocompatible materials which can bond the skin to the transdermally absorbable preparation, preferably pressure-sensitive adhesives, more preferably polyacrylate, polydimethylsiloxane, polyisobutylene or a combination thereof. Furthermore, the constituent materials of the adhesive layer may appropriately be incorporated with additives such as a well-known tackifier. The materials described above may also used as an auxiliary adhesive mass which is added to the surface of the drug permeable membrane.

Furthermore, the contact area of the adhesive layer with the skin can be appropriately determined by taking the area of the drug permeable membrane, the dosage period, the application site and the like into consideration.

Process for Producing

The process for producing the transdermally absorbable preparation according to the present invention is described in the following.

First, a plaster solution obtained by mixing the materials which comprise a drug containing layer is coated on a liner. Next, the plaster solution is dried at a temperature of about 60-120° C. to give the drug containing layer, on which the support layer is laminated. The liner is then removed from the drug containing layer, and an outer membrane is laminated on one side of the drug containing layer which had the liner disposed thereon to give a laminate. A cover layer on one side of which an adhesive layer is disposed is prepared. On this occasion, an inner layer having an inner hole may further be disposed on the adhesive layer, if desired. Subsequently, the laminate excluding the skin contact area is covered with the cover layer to give a transdermally absorbable preparation. On this occasion, the position and size of a fixing means are preliminarily configured so that the adhesive layer is placed at the peripheral or terminal regions of the skin contact area of the outer membrane. In addition, if an inner layer is provided, it is preliminarily set up so that the inner layer is between the support layer and the adhesive layer and extends outward from the peripheral region of the support layer, and the adhesive layer and the drug containing layer are separated on application.

In the process described above, solvents used in the preparation of the drug containing layer and the adhesive layer include for example ethyl acetate, butyl acetate, toluene, n-hexane, n-heptane, tetrahydrofuran, dimethylformamide, methanol or ethanol.

Application

The transdermally absorbable preparation according to the present invention is capable of stably and efficiently administering a drug to a living body and thus preferably used for diseases which require the administration of a drug for a long period.

In addition, the transdermally absorbable preparation may be set up at a single application or administered over a long period, preferably for 3-7 days, and more preferably for about 1 week. Specific regimen is appropriately determined by those skilled in the art depending on the drugs, the conditions of patients, the period of dosage, the sizes of preparations, and the like.

Furthermore, the living bodies to which the transdermally absorbable preparations according to the present invention are applied include, for example, rabbits, dogs or humans, preferably humans.

EXAMPLES

The present invention is now described more specifically with reference to examples, but it is not limited thereto.

Example 1

Preparation of a Transdermally Absorbable Preparation (without Inner Layer)

Preparation of Laminate
Formulation: Drug Containing Layer

TABLE 1

| Ingredient | % by mass |
| --- | --- |
| Bisoprolol fumarate | 25 |
| Aminoalkyl methacrylate copolymer E | 20 |
| Triethyl citrate | 10 |
| Isopropyl myristate | 10 |
| Oleyl alcohol | 5 |
| Duro-Tak ™ 387-2516 | 30 |

Outer membrane: Microporous polypropylene membrane (Celgard ™ 2400, Celgard)

Bisoprolol fumarate (Parmachem Asia), aminoalkyl methacrylate copolymer E (Degussa), triethyl citrate (Wako Pure Chemical Industries, Ltd.), isopropyl myristate (Nikko Chemicals Co., Ltd.) and oleyl alcohol (Kokyu Alcohol Kogyo Co., Ltd.) were prepared in the amounts described above and mixed by agitation in an appropriate amount of ethyl acetate. To the mixture thus obtained was added Duro-Tak™ 387-2516 (National Starch & Chemical) in a proportion described in the formulation to give a plaster solution.

The plaster solution was coated on a polyethylene terephthalate liner and dried at 70° C. for 15 minutes to give a drug containing layer. The drug containing layer after drying was adjusted to a weight of 100 g/m$^2$.

Next, a support layer (Scotchpak™ 9732, 3M) was laminated on the reverse side to the liner of the drug containing layer. The liner was then removed from the drug containing layer, which was sticked to a microporous polypropylene membrane (outer membrane) to give a laminate.

Provision of Fixing Means

Duro-Tak™ 87-2287 (National Starch & Chemical) was coated on a polyethylene terephthalate liner and dried at 80° C. for 15 minutes to give an adhesive layer. The adhesive layer after drying was adjusted to a weight of 100 g/m$^2$. Next, a cover layer (polyester woven fabric) was laminated on the reverse side to the liner of the adhesive layer to give a fixing means.

The liner was then removed from the adhesive layer of the fixing means, and the support layer of the laminate having been preliminarily cut out to a size of 45×45 mm and the adhesive layer of the fixing means were sticked together. Next, a polyethylene terephthalate liner was sticked to the surface formed by the adhesive layer and the microporous polypropylene membrane and cut out after adjusting the skin contact area to give a transdermally absorbable preparation (shape: square, 65×65 mm).

Example 2

Preparation of Transdermally Absorbable Preparation (without Inner Layer)

Preparation of Laminate
Formulation: Drug Containing Layer

TABLE 2

| Ingredient | % by mass |
| --- | --- |
| Bisoprolol fumarate | 30 |
| Aminoalkyl methacrylate copolymer E | 24.1 |
| Triethyl citrate | 10 |
| Isopropyl myristate | 10 |
| Duro-Tak ™ 387-2516 | 25.9 |

Outer membrane: Microporous polypropylene membrane (Celgard ™ 2400, Celgard)

Bisoprolol fumarate (Parmachem Asia), aminoalkyl methacrylate copolymer E, triethyl citrate, and isopropyl myristate were prepared in the amounts described above and mixed by agitation in an appropriate amount of ethyl acetate. To the mixture thus obtained was added Duro-Tak™ 387-2516 (National Starch & Chemical) in a proportion described in the formulation to give a plaster solution.

The plaster solution was coated on a polyethylene terephthalate liner and dried at 70° C. for 15 minutes to give a drug containing layer. The drug containing layer after drying was adjusted to a weight of 100 g/m$^2$.

Next, a support layer (Scotchpak™ 9732, 3M) was laminated on the reverse side to the liner of the drug containing layer. The liner was then removed from the drug containing layer, which was sticked to a microporous polypropylene membrane (outer membrane) to give a laminate (10 cm$^2$). Subsequently, a fixing means was prepared in the same manner as in Example 1 and disposed on the laminate to give a transdermally absorbable preparation.

Example 3

Preparation of Transdermally Absorbable Preparation (without Inner Layer)

Preparation of Laminate
Formulation: Drug Containing Layer

TABLE 3

| Ingredient | % by mass |
| --- | --- |
| Flurbiprofen | 20 |
| Isopropyl myristate | 10 |
| Glycerin | 10 |
| Sorbitan monolaurate | 5 |
| Duro-Tak ™ 87-2194 | 55 |

Outer membrane: Microporous polypropylene membrane (Celgard ™ 2400, Celgard)

Flurbiprofen, isopropyl myristate, glycerin and sorbitan monolaurate were mixed in a proportion described in the above formulation and dispersed uniformly. Next, To the mixed solution thus obtained was added Duro-Tak™ 87-2194 (National Starch & Chemical) in a proportion described in the above formulation to give a plaster solution.

The plaster solution was coated on a polyethylene terephthalate liner and dried at 80° C. for 15 minutes to give a drug containing layer. The drug containing layer after drying was adjusted to a weight of 100 g/m².

Next, a support layer (Scotchpak™ 9732, 3M) was laminated on the reverse side to the liner of the drug containing layer. The liner was then removed from the drug containing layer, and the drug containing layer and a microporous polypropylene membrane were laminated to give a laminate.

Subsequently, a fixing means was prepared in the same manner as in Example 1 and disposed on the laminate to give a transdermally absorbable preparation.

Example 4

Preparation of Transdermally Absorbable Preparation (having an Inner Layer)

First, an inner layer having square holes (Scotchpak™ 9732; 50 mm×50 mm, hole; 40 mm×40 mm) was prepared, and the inner layer and the adhesive layer of the fixing means (65 mm×65 mm) prepared in the same manner as in Example 1 were sticked together. Next, the support layer of the laminate (45 mm×45 mm) prepared in the same manner as in Example 1 and the inner layer were sticked together to give a transdermally absorbable preparation. In this connection, the inner layer in this transdermally absorbable preparation was arranged so that it extends outward from the peripheral region of the support layer, which is directly in contact with the adhesive layer of the fixing means through the holes in the inner layer.

Example 5

Preparation of Transdermally Absorbable Preparation (having an Inner Layer)

First, an inner layer having square holes (Scotchpak™ 9732; 50 mm×50 mm, hole; 40 mm×40 mm) was prepared, and a foam tape (65 mm×65 mm) was prepared as a fixing means. Then, the inner layer and the adhesive layer of the foam tape were sticked together. Next, the support layer of the laminate (45 mm×45 mm) prepared in the same manner as in Example 1 and the inner layer were sticked together to give a transdermally absorbable preparation. In this connection, the inner layer in this transdermally absorbable preparation was arranged so that it extends outward from the peripheral region of the support layer, which is directly in contact with the adhesive layer of the foam tape through the holes in the inner layer.

Referential Example 1

Reservoir Type Transdermally Absorbable Preparation

Formulation 4: Adhesive layer

TABLE 4

| Ingredient | % by mass |
| --- | --- |
| Duro-Tak ™ 387-2516 | 85 |
| Isopropyl myristate | 10 |
| Oleyl alcohol | 5 |

Duro-Tak™ 387-2516, isopropyl myristate and oleyl alcohol were mixed in a proportion described in Formulation 4 to give a plaster solution.

The plaster solution was coated on a polyethylene terephthalate liner so as the weight after drying to be 50 g/m2 and dried at 70° C. for 10 minutes to give an adhesive layer.

The adhesive layer was sticked on the outer membrane of the laminate obtained in the process of Example 1 to give a reservoir type transdermally absorbable preparation.

Test Example 1

In Vitro Skin Permeability Test in Hairless Mice

The laminate obtained in the processes of Examples 1-3 or the reservoir type transdermally absorbable preparation of Referential Example 1 (with an application area of 4.5 cm2, respectively) was arranged on the corneal layer of epidermis of hairless mice (7 weeks, female, n=3) and set up on a flow-through-cell through which warm water was circulated so that the skin surface is maintained at a temperature of about 32° C. Phosphate buffer physiological saline (pH 7.4) was used as a receiver solution, which was collected every 2 hours in an amount of 5 ml/hr for 24 hours. The flow rate of the solution thus collected was measured, and the amount of the drug was measured by HPLC. The skin permeation rate per hour and the drug utilization ratio in the drug containing layer (24 hours in total) were calculated from the results thus obtained The skin permeation rates and the drug utilization ratios of the laminated bodies in Example 1-3 are shown in Table 1. The skin permeation rates and the drug utilization ratios of the laminated bodies in Example 1-3 were higher as compared with those of the reservoir type transdermally absorbable preparation in Referential Example 1.

TABLE 5

Table 1

| Preparation | Skin permeation rate (mcg/cm²/hr) | Drug utilization ratio in preparation (%) |
|---|---|---|
| Referential Example 1 | 21.42 | 15.76 |
| Example 1 | 34.65 | 26.87 |
| Example 2 | 38.68 | 24.35 |
| Example 3 | 28.50 | 27.65 |

Test Example 2

In vitro Skin Permeability Test in Humans

The laminate (with an application area of 4.5 cm²) of Example 2 was arranged on the corneal layer of epidermis of humans and set up on a flow-through-cell through which warm water was circulated so that the skin surface is maintained at a temperature of about 32° C. Phosphate buffer physiological saline (pH 7.4) was used as a receiver solution, which was collected every 2 hours in an amount of 5 ml/hr for 168 hours. The flow rate of the solution thus collected was measured, and the amount of the drug was measured by HPLC. The skin permeation rate per hour and the drug utilization ratio in the drug containing layer (1 week in total) were calculated from the results thus obtained.

The skin permeation rate per hour and the drug utilization ratio in the preparation (1 week in total) are shown in Table 2.

Figure 4:
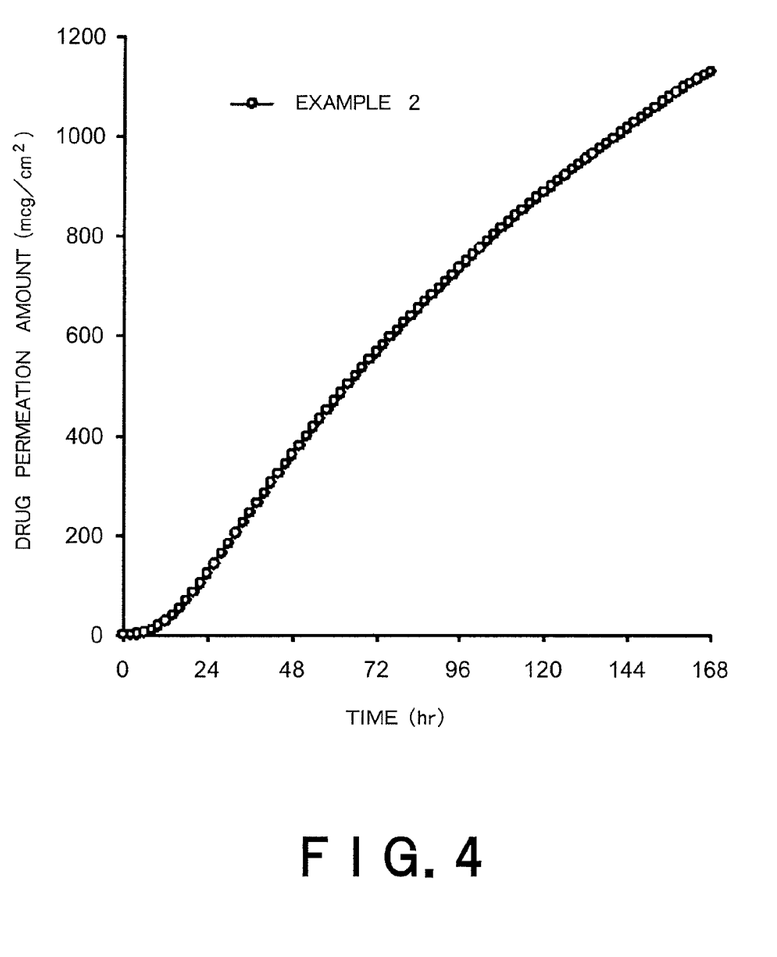
FIG. 4 is a graph which shows the result of an in vitro permeation test through human skin with the transdermally absorbable preparation according to the present invention.

Further, the cumulative drug permeation amount is shown in FIG. 4. It has been confirmed that the laminate of Example 2 releases the drug in an approximately constant skin permeation rate for 1 week (168 hours).

TABLE 6

Table 2

| Preparation | Skin permeation rate (mcg/cm2/hr) | Drug utilization ratio in preparation (%) |
|---|---|---|
| Example 2 | 10.50 | 37.25 |

Test Example 3

Confirmation of Stability of Transdermally Absorbable Preparations on the Skin

Preparation of Placebo Preparation (having an Inner Layer)

A placebo preparation was prepared in the same procedure as in Example 4 but bisoprolol fumarate was excluded from the formulation of the drug containing layer.

Patch Test

The placebo preparation was applied to the left or right side of breast in four adult male subjects for 1 week. During the test, the subjects had a shower every 24 hours.

After initiating the patch test, the rate of the area actually adhered to the skin (degree of adhesion) to the application area of the placebo preparation was measured every 24 hours (before shower) according to the following equation.

(Degree of adhesion)=(Area actually adhered to the skin)/(Application area of placebo preparations)×100  [Equation 1]

Figure 5:
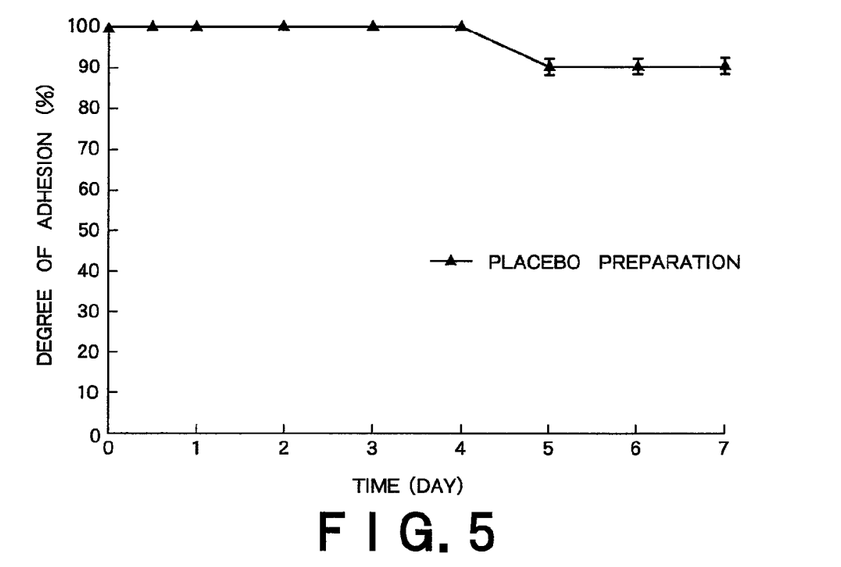
FIG. 5 is a graph which shows the result of a patch test with the transdermally absorbable preparation according to the present invention.

The result is shown in FIG. 5.

The placebo preparation having the inner layer described above maintained a degree of adhesion of at least 90% for 1 week.

Test Example 4

Storage Stability of Transdermally Absorbable Preparation 4-1: Storage Stability Test The transdermally absorbable preparation having an inner layer of Example 5 was selected as the test object and enclosed in an aluminum packaging bag for storing at 40° C. for one month. The drug release rates of the transdermally absorbable preparation before and after storage were measured by the technique described in the following.

First, deaerated pure water (900 ml) was prepared as the test liquid and poured into a container for eluent while maintaining the temperature of the liquid at 32±0.5° C. Next, the transdermally absorbable preparations before and after storage were prepared, and the one side as the support layer side of the transdermally absorbable preparation and the surface of the lower end of the rotating cylinder in an elution tester (VK7010, Vankel) were sticked together with a double-coated tape (Nicetack™, Nichiban Co., Ltd.), and the liner of the transdermally absorbable preparation was removed. Next, the distance between the lower end of the rotating cylinder and the inner bottom of the eluent container was fixed to 25±2 mm, and the rotating speed of the rotating cylinder was set up to 50/min for the elution test according to the Japanese Pharmacopoeia, 14 ed.

A 5 ml portion of the test liquid was collected at 1, 3, 6, 12, and 24 hours after initiating the test, and the test solution was supplemented with the test liquid immediately after collection.

The amounts of bisoprolol fumarate released at respective sampling times were measured by HPLC, and the release rate of bisoprolol fumarate was calculated on the basis of the amount of drug in the transdermally absorbable preparation.

Figure 6:
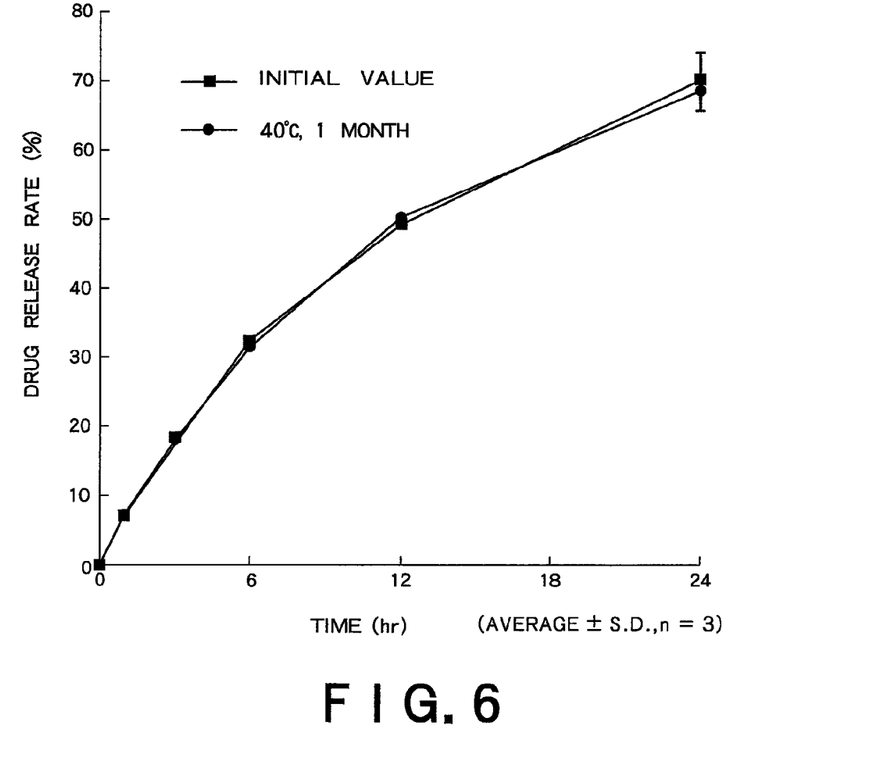
FIG. 6 is a graph which shows the result of an elution test of the transdermally absorbable preparation according to the present invention before and after one month storage at 40° C.

The result is shown in FIG. 6.

When the transdermally absorbable preparation having an inner layer in Example 5 was used, no significant decrease in the release rate of bisoprolol fumarate after storage for one month at 40° C. was observed as compared with the initial value (before storage at 40° C. for 1 month) and the storage stability of the transdermally absorbable preparation described above was confirmed.

What is claimed is:

1. A transdermally absorbable preparation comprising a laminate which comprises, in the order from the skin-contacting side, an outer membrane, a drug containing layer and a support layer;

a fixing component covering said laminate for fixing the laminate on the skin, which comprises, in the order from the skin-contacting side, an adhesive layer and a cover layer; and an inner layer which has an inner hole, and is provided between said support layer and said adhesive layer and extends outward from the peripheral region of said support layer, wherein:

said outer membrane is a microporous membrane having drug permeable pores, ensures controlled release of the drug into the skin, and is provided on the skin-contacting surface, said inner layer and said support layer comprise a drug impermeable material, said adhesive layer comprises a pressure-sensitive adhesive, said adhesive layer is directly contacted with one side of the support layer surrounded with said inner layer via said inner hole and fixes said laminate, and said inner layer is capable of separating said adhesive layer and the lateral side of said drug containing layer on the application of said transdermally absorbable preparation.

2. The transdermally absorbable preparation according to claim 1, wherein said inner layer and said support layer comprise at least one material selected from the group consisting of polyethylene terephthalate, polyester, polyethylene, polyurethane, polyamide, polypropylene, and ethylene-vinyl acetate copolymers.

3. The transdermally absorbable preparation according to claim 1, wherein said drug permeable polymer membrane comprises at least one material selected from the group consisting of ethylene-vinyl acetate copolymer, polyethylene, polypropylene, polyacrylonitrile, polymethyl methacrylate and a crosslinked polymer thereof.

4. The transdermally absorbable preparation according to claim 1, wherein said drug containing layer comprises a drug in an amount of 15% by mass or more of said drug containing layer.

* * * * *